(12) United States Patent
Burkart et al.

(10) Patent No.: US 6,348,612 B1
(45) Date of Patent: Feb. 19, 2002

(54) CHIRAL AMIDO-PHOSPHINE-PHOSPHINITE COMPOUNDS

(75) Inventors: Wolfgang Burkart, Grenzach-Wyhlen (DE); Michelangelo Scalone, Birsfelden; Rudolf Schmid, Basel, both of (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/035,554

(22) Filed: Mar. 5, 1998

(30) Foreign Application Priority Data

Mar. 10, 1997 (EP) .............................. 97103963
Jan. 23, 1998 (EP) .............................. 98101128

(51) Int. Cl.$^7$ .............................. C07F 9/141; C07F 9/22
(52) U.S. Cl. .................. 558/157; 558/155; 564/12; 549/491
(58) Field of Search .................. 564/12; 558/155, 558/157; 549/491

(56) References Cited

FOREIGN PATENT DOCUMENTS

EP    0 443 923    2/1991

OTHER PUBLICATIONS

A. Roucoux, F. Agbossou, A. Morteux. Francis Petit, New Alkylarylamidophosphinephosphinites as Chiral Diphosphines for Asymmetric Hydrogenation of Activated Keto Compounds, Tetrahedron:Asymetry 4, pp. 2279–2282 (1993).

Y. Ng Cheong Chan, D. Meyer, J. A. Osborn, Chemoselective Hydrogenation of Imines catalysed by Ir$^{III}$ Complexes, J. Chem. Soc., Chem. Commun. pp. 869–871 (1990).

R. Sablong and J. A. Osborn, Asymmetric Hydrogenaton of Imines Catalysed by Carboxylato (diphosphine)iridium (III) Complexes, Tetrahedron Asymmetry 7, pp. 3059–3062 (1996).

F. Hapiot, F. Agbossou, A. Mortreux, Asymmetric Catalytic Hydrogenation of α–Ketoesters Using New Chiral Ru(II) (AMPP) Complexes, Tetrahedron Asymmetry 6, pp. 11–14 (1995).

E. Negishi, T. Takahashi, K. Akiyoshi, 'Bis(triphenylphosphine)palladium:' Its Generation, Characterization, and Reactions, J. Chem. Soc., Chem. Commun., pp. 1338–1339 (1986).

C. E. Housecroft, B. A. M. Shaykh, A. L. Rheingold, B. S. Haggerty, Reactivity of Palladium (II) Complexes with Bidentate Bis(phosphine) Ligands toward the Octahydrotriborate(1–) Anion and Dependence of the Reaction upon Halide Arrangement: Molecular Structure of the trans–(bis-(diphenylphosphino)hexane)palladium(II) Dichloride Dimer, Inorg. Chem. 30, pp. 125–130 (1991).

Z. Jiang, A. Sen, Tailored Cationic Palladium (II) Compounds as Catalysts for Highly Selective Dimerization and Polymerization of Vinylic Monomers: Synthetic and Mechanistic Aspects, Organometallics 12, pp. 1406–1415 (1993).

A. Roucoux, L. Thieffry, J.–F. Carpentier, M. Devocelle, C. Meliet, F. Agbossou, A. Mortreux, Amidophosphine–Phosphinites: Synthesis and Use in Rhodium–Based Asymmetric Hydrogenation of Activated Keto Compounds. Crystal Structure of Bis [(μ–chloro)((S)–2–((diphenylphosphino)oxy)–2–phenyl–N–(diphenylphosphino)–N–methylacetamide)rhodium(I)], Organometallics 15, pp. 2440–2449 (1996).

I. Ojima, Catalytic Asymmetric Synthesis, pp. 1–39 (1993).

A. Roucous, M. Devocelle, J.–F. Carpentier, F. Agbossou, A. Mortreux, Highly Efficient Asymmetric Hydrogenation of Activated and Unactivated Ketones Catalyzed by Rhodium (I) Aminophosphine– and Amidophosphine–Phosphinite Complexes. Beneficial Effect of the Non Chiral Ligand, Synlett, pp. 358–360 (1995).

(List continued on next page.)

Primary Examiner—Jean F. Vollano
(74) Attorney, Agent, or Firm—Bryan Cave LLP

(57) ABSTRACT

Novel chiral amidophosphine-phosphinite compounds, which are present in (R) and (S) form, of the general formula

I

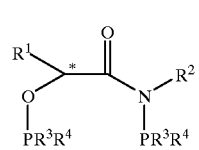

wherein $R^1$ signifies alkyl, cycloalkyl or aralkyl, $R^2$ signifies alkyl, cycloalkyl, aralkyl or aryl and $R^3$ and $R^4$ each independently signify alkyl, cycloalkyl, aralkyl, aryl or heteroaryl or $R^3$ and $R^4$ together with the respective phosphorus atom signify a 9-dibenzophospholyl, 9-phosphabicyclo[3.3.1]nonyl or 9-phosphabicyclo[4.2.1]nonyl group and * denotes a chiral center, are manufactured by reacting a compound of the general formula $R^1C(OH)$—$CONHR^2$ (III) with a disubstituted chlorophosphane of the general formula $R^3R^4PCl$ (IV) in a solvent and in the presence of a base. As ligands the amidophosphine-phosphinite compounds in accordance with the invention form complexes with Group VIII transition metals, especially with rhodium, iridium, ruthenium and palladium, and optionally with further ligands, and such complexes are likewise an object of the present invention; they can be used as catalysts for enantioselective reactions, especially for asymmetric hydrogenations, enantioselective hydrogen displacements and allylic substitution reactions.

54 Claims, No Drawings

OTHER PUBLICATIONS

R. R. Schrock, J. A. Osborn, Coordinatively Unsaturated Cationic Complexes of Rhodium (I), Iridium(I), Palladium(II), and Platinum (II). Generation, Synthetic Utility, and Catalytic Studies, Communications to the Editor, J. Am. Chem. Soc., pp. 3089–3091 (1971).

Derwent Abstract 443923.

CA:125:11069 abs of Organometallics by Roucoux et al 15(10) pp 2440–9, 1996.*

CA:123:227358 abs of Synlett by Roucoux et al (4) pp 358–60, 1995.*

* cited by examiner

CHIRAL AMIDO-PHOSPHINE-PHOSPHINITE COMPOUNDS

BACKGROUND OF THE INVENTION

Enantiomerically pure (R) or (S) compounds can be produced by causing compounds to undergo enantioselective reactions. Use of enantioselective catalysts which are capable of catalyzing asymmetric hydrogenations, enantioselective hydrogen displacements and allylic substitution reactions, among others, can facilitate the attainment of high optical yields. The present invention relates to novel chiral amidophosphine-phosphinite compounds and complexes of these compounds as ligands with Group VIII metals, which complexes may be used as enantioselective catalysts.

SUMMARY OF THE INVENTION

The present invention is concerned with novel chiral, amido-phosphine-phosphinite compounds, which are present in (R) or (S) form, of formula (I)

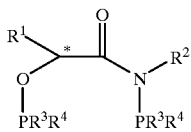

I wherein $R^1$ signifies $C_{2-8}$-alkyl, $C_{3-8}$-cycloalkyl or aryl-$C_{1-4}$-alkyl, $R^2$ signifies $C_{1-8}$-alkyl, $C_{3-8}$-cycloalkyl, aryl-$C_{1-4}$-alkyl or aryl and $R^3$ and $R^4$ each independently signify $C_{1-8}$-alkyl, $C_{3-8}$-cycloalkyl, aryl-$C_{1-4}$-alkyl, aryl or heteroaryl or $R^3$ and $R^4$ together with the respective phosphorus atom signify a 9-dibenzophospholyl, 9-phosphabicyclo[3.3.1]nonyl or 9-phosphabicyclo[4.2.1]nonyl group and

* denotes a chiral center.

The invention is also concerned with the manufacture of the amidophosphine-phosphinite compounds of formula I, complexes of these compounds as ligands with Group VIII metals and optionally with additional ligands as well as the use of the complexes as catalysts for enantioselective reactions such as e.g. asymmetric hydrogenations, enantioselective hydrogen displacements, allylic substitution reactions and the like.

The object of the present invention is to provide novel, chiral amidophosphine-phosphinite compounds which can be used in the form of the aforementioned complexes in enantioselective reactions and thereby facilitate high optical yields. The object is achieved by the chiral amidophosphine-phosphinite compounds of formula I.

DETAILED DESCRIPTION OF THE INVENTION

The following definitions of the general terms are used in the present specification and apply irrespective of whether the terms appear as such or in combination.

The term "$C_{1-4}$-alkyl", "$C_{1-8}$-alkyl" or "$C_{2-8}$-alkyl" signifies in the scope of the present invention a straight-chain or branched alkyl group with up to 4 or 8 carbon atoms such as, for example, methyl, ethyl, propyl, isopropyl, butyl, isobutyl, tert. butyl, pentyl, isopentyl, neopentyl, hexyl, tert. hexyl, heptyl, isoheptyl, octyl or isooctyl.

The term "$C_{3-8}$-cycloalkyl" embraces cyclopropyl, cyclobutyl, cyclopentyl, cyclohexyl, cycloheptyl and cyclooctyl.

The term "aryl", alone or as part of "aryl-$C_{1-4}$-alkyl", signifies a phenyl or naphthyl group which in each case can be either unsubstituted or mono- or multiply-substituted. Substituents which come into consideration here are halogen, $C_{1-8}$-alkyl and $C_{1-8}$-alkoxy groups, halogenated $C_{1-8}$-alkyl and $C_{1-8}$-alkoxy groups, di($C_{1-8}$-alkyl)amino, tri($C_{1-4}$-alkyl)silyl (preferably trimethylsilyl) and phenyl, whereby several substituents present can be the same or different. In the case of "aryl-$C_{1-4}$-alkyl" this preferably signifies unsubstituted benzyl.

The term "halogen" signifies fluorine, chlorine, bromine or iodine.

The term "heteroaryl" signifies a 5- or 6-membered heterocyclic group having aromatic character, which has in the ring one or more hetero atoms from the group of nitrogen, oxygen and sulfur. Examples of 5-membered heterocyclic groups are pyrrolyl, thienyl and furyl, with pyridyl being an example of a 6-membered heterocyclic group. Moreover, the heterocyclic groups can be substituted in the same manner as the aryls set forth above and/or can have a fused benzene ring. Preferably, heteroaryl has no substituents.

The term "$C_{1-8}$-alkoxy" signifies a straight-chain or branched alkoxy group with up to 8 carbon atoms, preferably with up to 4 carbon atoms.

Methoxy, ethoxy, propoxy, isopropoxy and butoxy are examples.

The term "halogenated $C_{1-8}$-alkyl" or "halogenated $C_{1-8}$-alkoxy" signifies an alkyl or alkoxy group which in each case is substituted with one or more halogen atoms, especially chlorine or fluorine. Examples are trifluoromethyl, trichloromethyl and pentafluoromethyl and, respectively, fluoromethoxy and chloromethoxy.

Amidophosphine-phosphinite compounds of formula I are preferred in which independently of one another $R^1$ signifies tert. butyl, $R^2$ signifies methyl and $R^3$ and $R^4$ each signify cyclohexyl, phenyl, 3-5-xylyl, 3,5-di(trifluoromethyl)phenyl, 3,5-di(tert. butyl)phenyl, 3,5-di(tert. butyl)-4-methoxyphenyl or 2-furyl or $R^3$ and $R^4$ together with the phosphorus atom signify 9-dibenzophospholyl.

Preferably, $R^3$ and $R^4$ have the same significance.

Amidophosphine-phosphinite compounds of formula I in which $R^3$ and $R^4$ signify 3,5-di(tert. butyl)phenyl are especially preferred.

Particularly preferred amidophosphine-phosphinite compounds of formula I are:

(S)- or (R)-N-(Diphenylphosphanyl)-2-[(diphenylphosphanyl)oxy]-3,3,N-trimethyl-butyramide, (S)- or (R)-N-(dicyclohexylphosphanyl)-2-[(dicyclohexylphosphanyl)-oxy]3,3,N-trimethyl-butyramide, (S)- or (R)-N-[di-(2-furyl)-phosphanyl]-2-[(di-(2-furyl)-phosphanyl)oxy]-3,3,N-trimethyl-butyramide, (S)- or (R)-N-(5H-dibenzophospholyl)-2-[(5H-dibenzophospholyl)oxy]-3,3,N-trimethyl-butyramide, (S)- or (R)-N-[bis(3,5-dimethylphenyl)-phosphanyl]-2-[(bis(3,5-dimethylphenyl)-phosphanyl)oxy]-3,3,N-trimethyl-butyramide, (S)- or (R)-N-[bis(3,5-di(trifluoromethyl)phenyl)-phosphanyl]-2-[(bis(3,5di(trifluoromethyl)phenyl)-phosphanyl)oxy]-3,3,N-trimethyl-butyramide, (S)- or (R)-N-[bis(3,5-di(tert. butyl)phenyl)-phosphanyl]-2-[(bis(3,5-di-(tert. butyl)phenyl)-phosphanyl)oxy]-3,3,N-trimethyl-butyramide and (S)- or (R)-N-[bis(3,5-di(tert. butyl)-4-methoxyphenyl)-phosphanyl]-2-[(bis(3,5-di(tert. butyl)-4-methoxyphenyl)-phosphanyl)oxy]-3,3,N-trimethyl-butyramide.

The amidophosphine-phosphinite compounds of formula I in accordance with the invention (in the role of ligands) form complexes with transition metals of Group VIII, especially with rhodium, iridium, ruthenium and palladium, and such complexes are likewise an object of the present invention; they can be used as catalysts for enantioselective reactions, especially for Aasymmetric hydrogenations, enantioselective hydrogen displacements and allylic substitution reactions.

These complexes in accordance with the invention of the compounds of formula I with transition metals of Group VIII can contain further ligands. Examples of such complexes, which are likewise in accordance with the invention, are especially optically active cationic and neutral rhodium, iridium, ruthenium and palladium complexes of formulas

| | |
|---|---|
| $[Rh(Y)(L)_n]^+A^-$ | II-a |
| $[Rh(Y)(L)_nB]$ | II-b |
| $[Ir(Y)(L)_n]^+A^-$ | II-c |
| $[Ir(Y)(L)_nB]$ | II-d |
| $[Ir(Y)(B)_4]^-_rM^{r+}$ | II-e |
| $[IrH(Y)(B)_2]$ | II-f |
| $[Ir(Y)(B)_3]_2$ | II-g |
| $[Ir(B)_3(Y)]$ | II-h |
| $[Ru(Y)]^{2+}(A^-)_2$ | II-i |
| $[Ru(Y)(B)_2]$ | II-j |
| $[Ru(Y)(C^1)(C^2)_{2-m}](C^3)_m$ | II-k |
| $[Pd(Y)(B)_2]$ | II-l |
| $[Pd(Y)_2]$ | II-m |
| $[Pd(Y)(L)_n]^{2+}(A^-)_2$ | II-n | wherein
L signifies a neutral ligand,
$A^-$ signifies an anion of an oxygen acid or complex acid,
B signifies an anionic coordinating ligand,
$C^1$ signifies benzene, p-cymene, xylene or hexamethylbenzene,
$C^2$ signifies halogen,
$C^3$ signifies halogen or $A^-$,
n signifies 0, 1 or 2,
m signifies 0, 1 or 2,
r signifies 1 or 2,
$M^{r+}$ signifies an alkali metal or alkaline earth ion or a tetra-substituted ammonium ion (r is 1,2 or, respectively, 1) from the group of $(C_{1-8}$-alkyl$)_4$ $N^+$,(phenyl)$N^+(C_{1-8}$-alkyl$)_3$, (benzyl)$N^+(C_{1-8}$-alkyl$)_3$, and
Y signifies a chiral amidophosphine-phosphinite compound of formula I.

The term "neutral ligand" (L) signifies an exchangeable ligand, especially an olefin, e.g. ethylene, propylene, cyclooctene, 1,5-hexadiene, norbornadiene or 1,5-cyclooctadiene; an aromatic, e.g. benzene, hexamethylbenzene or p-cymene; a nitrile, e.g. acetonitrile or benzonitrile; or a molecule of the solvent in which the complex is produced. This ligand can be exchanged in the hydrogenation. Where more than one such ligand is present (n=2), the ligands can be the same or different.

The term "oxygen acid or complex acid" (source of the anion $A^-$) signifies an acid from the group of $H_2SO_4$, $HClO_4$, $HBrO_4$, $HIO_4$, $HNO_3$, $H_3PO_4$, $H_3PO_3$ and $CF_3SO_3H$ or a halogen complex with the element boron, phosphorus, arsenic, antimony or bismuth. Preferred representatives of both types of acids are $HClO_4$, $CF_3SO_3H$, $HPF_6$, $HBF_4$, $HB(phenyl)_4$, $HB[3,5(CF_3)_2-C_6H_3]_4$, $HSbF_6$ and $HAsF_6$. The anion $A^-$ is formed in each case by removing a hydrogen ion; examples are ClO, PF and BF.

The term "anionic coordinating ligand" (B) embraces especially halogen, a carboxylic acid residue, a sulphonate residue, e.g. tosylate or methanesulphonate, a 1,3-diketonate, e.g. acetylacetonate, an optionally substituted phenolate, hydroxy, nitrate, nitrite, cyanate, rhodanide, cyanide, allyl and 2-methylallyl. When phenolate is substituted, $C_{1-4}$-alkyl groups and halogen atoms especially come into consideration as substituents, with the substitution being single or multiple.

As the alkali metal ion ($M^+$) or alkaline earth metal ion ($M^{2+}$) there is especially suitable the sodium or potassium ion or, respectively, the calcium or magnesium ion.

The term "tetrasubstituted ammonium ion" ($M^+$) signifies an anion consisting of a nitrogen atom and four identical or different substituents which are selected from the group of $C_{1-8}$-alkyl, phenyl and benzyl, such as, for example, the anions $(C_{1-8}$-alkyl$)_4N^+$, (phenyl)$N^+(C_{1-8}$-alkyl$)_3$ and (benzyl)$N^+(C_{1-8}$-alkyl$)_3$.

The term "halogen" (B, $C^2$ or $C^3$) embraces fluorine, chlorine, bromine and iodine. In the case of a complex of formula II-e in which B signifies halogen, the halogen can be derived from the corresponding alkali metal, alkaline earth metal or tetrasubstituted ammonium halide.

Preferred complexes in accordance with the invention of the compounds of formula I are the optically active cationic and neutral rhodium, iridium and ruthenium complexes of formulae II-a to II-k.

The process in accordance with the invention for the manufacture of the novel chiral compounds of formula I comprises reacting a compound of formula (III)

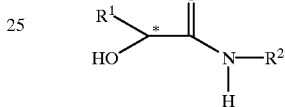

III wherein
  $R^1$ signifies $C_{2-8}$-alkyl, $C_{3-8}$-cycloalkyl or aryl-$C_{1-4}$-alkyl,
  $R^2$ signifies $C_{1-8}$-alkyl, $C_{3-8}$-cycloalkyl, aryl-$C_{1-4}$- alkyl or aryl, and
  * denotes a chiral center
with a disubstituted chlorophosphane of the general formula (IV)

$R^3R^4PCl$                                    IV wherein
  $R^3$ and $R^4$ each independently signify $C_{1-8}$-alkyl, $C_{3-8}$-cycloalkyl, aryl-$C_{1-4}$-alkyl, aryl or heteroaryl or $R^3$ and $R^4$ together with the phosphorus atom signify a 9-dibenzophospholyl, 9-phosphabicyclo[3.3.1]nonyl or 9-phosphabicyclo[4.2.1]nonyl group
in a solvent and in the presence of a base.

Suitably, the compound of formula III is dissolved in a solvent, preferably under an inert atmosphere, e.g. nitrogen or argon, and a base (the first) is added, which can usually be effected at room temperature. Then, the solution is cooled down considerably, suitably to about −80° C., and subsequently the second base is added thereto followed slowly by the chlorophosphane, suitably dissolved in a solvent. The reaction starts even at the low temperature. Subsequently, the temperature can be increased gradually, conveniently to room temperature, and thereafter the thus-obtained product (the compound of formula I) can be isolated and purified according to methods known per se.

In the process in accordance with the invention bases which serve in the role of the "first base" are secondary or tertiary amines, especially dialkylamines or trialkylamines, e.g. dimethylamine, diethylamine, dipropylamine, diisopropylamine, trimethylamine, triethylamine and tripropylamine, and bases which serve in the role of the "second base" are alkali metal alkyls or alkali metal aryls, e.g. propyllithium, butyllithium, phenyllithium, butylisodium and butylpotassium, i.e. a combination of a secondary or tertiary amine (first base) with an alkali metal alkyl or alkali metal aryl (second base). Diisopropylamine and butyllithium are especially preferred bases.

Suitable solvents are aliphatic hydrocarbons, preferably halogenated aliphatic hydrocarbons such as, for example, methylene chloride and chloroform; and aliphatic and cyclic ethers such as, for example, diethyl ether, tert. butyl methyl ether and 1,2-dimethoxyethane and, respectively, dioxan, furan and tetrahydrofuran; or mixtures of such solvents. Diethyl ether or tetrahydrofuran is preferably used as the solvent for the manufacture of the amidophosphine-phosphinite compounds.

For the isolation and purification of the product, the mixture is conveniently evaporated, the residue is taken up in a suitable solvent, especially in a lower aliphatic ether, e.g. diethyl ether, and, after removal of residual solid constituents by filtration, the filtrate is evaporated to dryness. The thusobtained chiral compound of formula I can be purified further by crystallization, especially from a lower aliphatic hydrocarbon, e.g. pentane.

The enantiomerically-pure (R)- or (S)-compounds of formula III in turn can be produced by the asymmetric hydrogenation of the corresponding α-ketoamide $R^1COCONHR^2$ using enantiomerically-pure hydrogenation catalysts in a manner known per se [H.Takaya et. al., "Asymmetric Hydrogenation", pages 1–39 in Catalytic Asymmetric Synthesis, Ed. Iwao Ojima, VCH Publishers, Inc., New York/Weinheim/Cambridge (1993) as well as the references cited at the end of the article].

It has surprisingly been found that the complexes of formulae II-a to II-n not only as such, i.e. in the form of the respective individual complex consisting of the ligands Y in accordance with the invention (the chiral amidophosphine-phosphinite compound of formula I), the group VIII metal and optionally further ligands, but also in the form of the individual components, act as catalysts for enantioselective reactions, e.g. asymmetric hydrogenations. The complexes of formulae II-a to II-n themselves can be produced from these components in a manner known per se: see, for example, J.A.C.S. 93, 3089–3091 (1971); J. Chem. Soc., Chem. Comm. 1990, 869–871; Tetr.: Asymm. 1(11), 3059–3062 (1996); ibid. 6(1), 11–14 (1995); F. R. Hartley, The Chemistry of Platinum and Palladium, Applied Science Publishers Ltd., London 1973; J. Chem. Soc., Chem. Comm. 1986, 1338–1339; Inorg. Chem. 30, 125–130 (1991); Organometallics 12, 1406–1415 (1993); as well as ibid 15, 2440–2449 (1996).

The complexes in accordance with the invention of the compounds of formula I with Group VIII metals, especially those of the aforementioned formulae II-a to II-k, are suitable, for example, for the catalysis of the asymmetric hydrogenation of compounds of formula V to compounds of formula VI

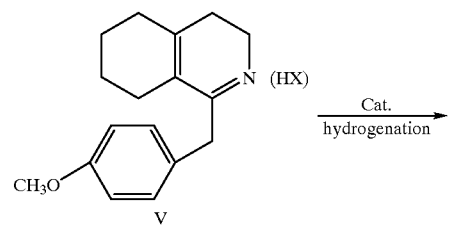

V

-continued

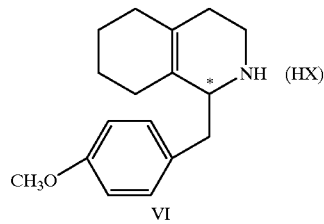

VI wherein HX signifies a mineral acid from the group of $HBF_4$, $H_2SO_4$, $HPF_6$, HCl, HBr, HI, $H_3PO_4$, $HSbF_6$, $HClO_4$ and $NaH_2PO_4$ or a strong organic acid from the group of $C_{1-8}$-alkyl$SO_3H$, picric acid, formic acid, lower alkyl- and arylcarboxylic acids, e.g. acetic acid, propionic acid and benzoic acid, and dicarboxylic acids e.g. oxalic acid, succinic acid, maleic acid and phthalic acid, and * denotes a chiral center.

The molar ratio (substrate:catalyst, commonly denoted as "SIC") between the compound of formula V to be hydrogenated and the metal complex which is used as the catalyst in accordance with any one of formulae II-a to II-k, conveniently lies between about 20 and about 80 000, preferably between about 500 and about 30,000. The hydrogenation is conveniently carried out at temperatures in the range of about 0° C. to about 150° C., preferably 10° C. to 100° C., and under a pressure of about 1 to about 200 bar (about 0.1 MPa to about 20 MPa), preferably 10 to 80 bar (1 MPa to 8 MPa).

The free base of the compounds of formula VI is a known and valuable intermediate for pharmaceutically usable end products, e.g. the antitussive dextromethorphan and the analgesic levorphanol.

The complexes in accordance with the invention are also suitable, for example, as catalysts for the asymmetric hydrogenation of compounds of formula VII to compounds of formula VIII

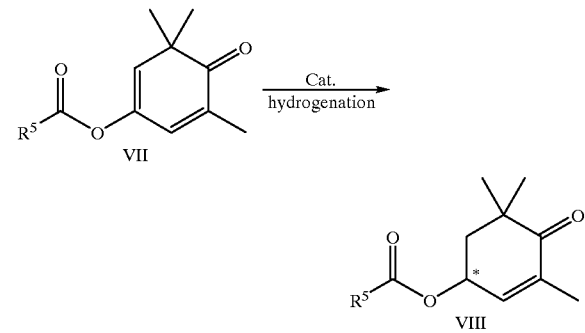

wherein $R^5$ signifies $C_{1-8}$-alkyl, $C_{1-8}$-alkyl, $C_{1-8}$-alkoxy, phenyl, benzyl or a group $N(R^6)_2$ and $R^6$ signifies hydrogen, $C_{1-8}$-alkyl, phenyl or benzyl and * denotes a chiral center.

Cationic rhodium complexes of formula II-a are preferably used as the catalysts for this asymmetric hydrogenation.

The ratio between rhodium and the ligands in accordance with the invention (chiral amidophosphine-phosphinite compound of formula I) lies in the range of about 0.05 to about 5 mol, preferably of 0.5 to 2 mol, of rhodium per mol of ligand. The molar ratio between the compound of formula VII to be hydrogenated and rhodium in the complex of formula II-a, i.e. the substrate:catalyst ratio (S/C), conveniently amounts to about 20 to about 100,000, especially about 500 to about 50,000. The enantioselective hydrogenation of compounds of formula VII using a complex of formula II-a can be effected at temperatures of about 10° C. to about 120° C., preferably at about 10° C. to about 60° C. The hydrogenation is conveniently effected under a pressure of about 1 to about 150 bar (about 0.1 to about 15 MPa), preferably of 5 to 60 bar (0.5 to 6 MPa).

The compounds of formula VIII are valuable intermediates for the synthesis of retinoids, which can be used e.g. for the therapy and prophylaxis of dermatological disorders, e.g. acne and psoriasis [see, for example, Pure & Appl. Chem. 57, 741 (1985) as well as European Patent Publication 0 802 181 A1]. Further, the compounds of formula VIII, which can be converted by hydrolysis into phorenol and in a further reaction step into optically active actinol, are important intermediates for the production of 3-hydroxy-carotenoids, especially for the production of zeaxanthin [see Pure & Appl. Chem. 51, 535–564 (1979) and Helv. Chim. Acta 63, 1451–1455 (1980)].

EXAMPLES

The following Examples serve to illustrate the invention in more detail and are not intended in any manner to represent a limitation. In the Examples the abbreviations have the following significance:

| | |
|---|---|
| GC | gas chromatography |
| HPLC | high pressure liquid chromatography |
| ee | enantiomeric excess |
| RT | room temperature |
| m.p. | melting point |
| HV | high vacuum |
| Ac | acetyl |
| OV/p-DiMe-β-CD | 2,6-dimethoxy-3-pentoxy-β-cyclodextrin dissolved in the achiral phase OV (product from Ohio Valley Chemicals, Marietta, OH, USA) |
| COD | 1,5-cyclooctadiene |
| BIPHEMP | (6,6'-dimethylbiphenyl-2,2'-diyl)bis(diphenylphosphine) |

Example 1

Preparation of (R)-2-hydroxy-3,3,N-trimethyl-buryramide (Compound of Formula III)

A catalyst solution was prepared in a glove box ($O_2$ content<1 ppm) by dissolving 385 mg (0.5 mmol) of [Ru(OAc)$_2$((R)-BIPHEMP)] in 40 ml of a 0.025 molar methanolic hydrochloric acid solution and 40 ml of methylene chloride, subsequently stirred at 20° C. for 1.5 hours and thereafter transferred into a pressure-tight catalyst supply vessel. A 2 l steel autoclave was charged with 71.6 g (0.5 mol) of 2-keto-3,3,N-trimethyl-butyramide and 310 ml of methanol and sealed. After replacement of the atmosphere with hydrogen the catalyst solution was allowed to flow from the catalyst supply vessel into the autoclave with slight over-pressure and the hydrogenation was carried out while stirring at 60° C. and at a pressure of 60 bar (6 MPa). After 20 hours the hydrogenation was interrupted and the reaction mixture was evaporated. From a solution of the residue in 250 ml of diisopropyl ether there firstly separated at room temperature 1.2 g of crystalline product with ee=3% and a melting point of 135–137° C. By adding 275 ml of cyclohexane and stirring the mixture in an ice bath for 3 hours there were isolated 43.9 g (60.5%) of (R)-2-hydroxy-3,3,N-trimethyl-butyramide; m.p. 69–71° C.; [α]=+61.0° (c=1, CHCl$_3$), ee=98.7% (measured by GC on an OV-61/p-DiMe-β-CD chiral column).

Example 2

Preparation of (S)-2-hydroxy-3,3,N-trimethyl-butyramide (Compound of Formula III)

The experiment was carried out in an analogous manner to Example 1. The asymmetric hydrogenation of 55.0 g (0.384 mol) of 2-keto-3,3,N-trimethyl-butyramide in 270 ml of methanol and 30 ml of methylene chloride in the presence of a catalyst prepared from 296 mg (0.384 mmol) of [Ru(OAc)$_2$((S)-BIPHEMP)] and 31 ml of a 0.025 molar methanolic hydrochloric acid solution gave, after crystallization, 34.4 g (62%) of (S)-2-hydroxy-3,3,N-trimethyl-butyramide, m.p.=60–62° C., [α]=−59.9° (c=1, CHCl$_3$), ee=99.2%.

Example 3

Preparation of (R)-N-(diphenylphosphanyl)-2-[(diphenylphosphanyl)oxy]-3,3,N-trimethyl-butyramide 3.88 g (26.7 mmol) of (R)-2-hydroxy-3,3,N-trimethyl-butyramide were dissolved in 200 ml of dried tetrahydrofuran at RT in a 500 ml flask having a valve cut into the side for argon gasification, a stirrer core and a serum stopper, and 0.5 ml of diisopropylamine was added using a syringe. After stirring for 30 minutes the colorless solution was cooled to about −78° C. and 28.5 ml (53.5 mmol) of butyllithium were added using a syringe during 10 minutes. After stirring at −78° C. for 1 hour the pale yellow suspension was treated dropwise with a solution of 11.8 g (53.5 mmol) of chlorodiphenylphosphane in 30 ml of tetrahydrofuran over 30 minutes, a pale yellow clear solution gradually forming after a further 60 minutes at −78° C. Subsequently, the cooling bath was removed, the solvent was evaporated at RT and the residual foam-like yellow oil was dried in a HV for 5 hours. A colorless suspension with a lithium chloride precipitate formed upon adding 200 ml of diethyl ether. The supernatant yellow solution was filtered over Alox (I, basic; aluminum oxide for chromatography, activity grade I, CAMAG, CH-4123 Muttenz, Switzerland) with diethyl ether in a protective gas suction filter. The combined filtrates were evaporated completely in a Schlenk tube in a HV and the residue was dried in a HV for 12 hours. The residual yellow oil was solidified with liquid nitrogen at about −180° C. and treated rapidly with 50 ml of pentane. Colorless crystals formed after ultrasound treatment for 5 minutes. After standing at about 5° C. for 24 hours the supernatant solution was separated and the white crystallizate was washed twice at 0° C. with 20 ml each time, a total of 40 ml, of pentane and dried in a HV for 2 hours. Yield: 8.41 g (61%) of (R)-N-(diphenylphosphanyl)-2-[(diphenylphosphanyl)oxy]-3,3,N-trimethyl-butyramide [(R)-tLANOP] as colorless crystals, m.p. 95–96° C., [α]=+37.5° (c=1, CHCl$_3$). $^{31}$P-NMR (δ, ppm): 52.5 (P-N), 115.7 (P-O).

Example 4

Preparation of (S)-N-(diphenylphosphanyl)-2-[(diphenylphosphanylsoxy]-3,3,N-trimethyl-butyramide Analogously to the synthesis described in Example 3, a mixture consisting of 4.47 g (30.7 mmol) of (S)-2-hydroxy-3,3,N-trimethyl-butyramide, 0.65 ml of diisopropylamine and 32.7 ml (61.6 mmol) of butyllithium in tetrahydrofuran was treated at about −78° C. with 13.6 g (61.6 mmol) of chlorodiphenylphosphane. Working up, purification and crystallization as described in Example 3 gave 10.6 g (20.6 mmol, 67%) of (S)-N-(diphenylphosphanyl)-2-[(diphenylphosphanyl)oxy]-3,3,N-trimethyl-butyramide [(S)-tLANOP] as colorless crystals, m.p. 95–96° C. [α]=−37.7° (c=1, CHCl$_3$), purity: 99% (NMR). $^{31}$P-NMR (δ, ppm): 52.5 (P-N), 115.7 (P-O).

Example 5

Preparation of (R)-N-[di-(2-furyl)-phosphanyl]-2-[(di-(2-furyl)-phosphanyl)oxy]-3,3,N-trimethyl-butyramide Analogously to the synthesis described in Example 3, a mixture consisting of 1.78 g (12.3 mmol) of (R)-2-hydroxy- 3,3,N-trimethyl-butyramide, 0.1 ml of diisopropylamine and 13.0 ml (61.6 mmol) of butyllithium in tetrahydrofuran was treated at about −78° C. with 4.93 g (24.6 mmol) of chloro-di(2-furyl)-phosphane. Working up, purification and crystallization as described in Example 3 gave 2.77 g (48%) of (R)-N-[di-(2-furyl)-phosphanyl]-2-[(di-(2-furyl)-phosphanyl)oxy]-3,3,N-trimethyl-butyramide [(R)-(2-furyl)-tLANOP] as a colorless, hydrolysis-sensitive powder, purity: ≧95% (NMR). $^{31}$P-NMR (δ, ppm): 0.8 (P-N), 64.9 (P-O).

Example 6

Preparation of (R)-N-(dicyclohexylphosphanyl)-2-[(dicyclohexylphosphanyl)oxy]-3,3,N-trimethyl-butyramide Analogously to the synthesis described in Example 3, a mixture consisting of 3.16 g (22.3 mmol) of (R)-2-hydroxy-3,3,N-trimethyl-butyramide, 0.50 ml of diisopropylamine and 27.8 ml (44.5 mmol) of butyllithium in tetrahydrofuran was treated at about −78° C. with 10.4 g (44.5 mmol) of chlorodicyclohexylphosphane. Working up, purification and crystallization as described in Example 3 gave 8.20 g (69%) of (R)-N-(dicyclohexylphosphanyl)-2-[(dicyclohexylphosphanyl)oxy]-3,3,N-trimethyl-butyramide [(R)-Cy-tLANOP] as a colorless solid, purity 98% (NMR). $^{31}$P-NMR (δ, ppm): 65.4 (P-N), 139.3 (P-O).

Example 7

Preparation of (S)-N-(dicyclohexylphosphanyl)-2-[(dicyclohexylphosphanyl)oxy]-3,3,N-trimethyl-butyramide Analogously to the synthesis described in Example 3, a mixture consisting of 1.69 g (11.9 mmol) of (S)-2-hydroxy-3,3,N-trimethyl-butyramide, 0.25 ml of diisopropylamine and 14.8 ml (23.7 mmol) of butyllithium in tetrahydrofuran was treated at about −78° C. with 5.52 g (23.7 mmol) of chlorodicyclohexylphosphane. Working up, purification and crystallization as described in Example 3 gave 4.20 g (66%) of (S)-N-(dicyclohexylphosphanyl)-2-[(dicyclohexylphosphanyl)oxy]-3,3,N-trimethyl-butyramide [(S)-Cy-tLANOP] as a colorless, hydrolysis-sensitive powder after crushing with a spatula, purity: 98% (NMR). $^{31}$P-NMR (δ, ppm): 65.4 (P-N), 139.3 (P-O).

Example 8

Preparation of (R)-N-[bis(3,5-dimethylphenyl)-phosphanyl]-2-[(bis(3,5-dimethylphenyl)-phosphanyl)oxy]-3,3,N-trimethyl-butyramide Analogously to the synthesis described in Example 3, a mixture consisting of 0.66 g (4.56 mmol) of (R)-2-hydroxy-3,3,N-trimethyl-butyramide, 0.05 ml of diisopropylamine and 5.70 ml (30.3 mmol) of butyllithium in tetrahydrofuran was treated at about −78° C. with 6.63 g (30.3 mmol) of chloro-bis(3,5-dimethylphenyl)phosphane. Working up, purification and crystallization as described in Example 3 gave 2.23 g (73%) of (R)-N-[bis(3,5-dimethylphenyl)-phosphanyl]-2-[(bis(3,5-dimethylphenyl)-phosphanyl)oxy]-3,3,N-trimethyl-butyramide [(R)-3,5-Xyl-tLANOP] as a colorless hydrolysis-sensitive powder. Purity: about 90–95% (NMR). $^{31}$P-NMR (δ, ppm): 53.3 (P-N), 117.7 (P-O).

Example 9

Preparation of (S)-N-[bis(3,5-di(trifluoromethyl)phenyl)-phosphanyl]-2-[(bis(3,5-di(trifluoromethyl)phenyl)-phosphanyl)oxy]-3,3,N-trimethyl-butyramide Analogously to the synthesis described Example 3, a mixture consisting of 0.76 g (5.26 mmol) of (S)-2-hydroxy-3,3,N-trimethyl-butyramide, 0.05 ml of diisopropylamine and 6.56 ml (10.5 mmol) of butyllithium in tetrahydrofuran was treated at about −78° C. with 6.63 g (10.5 mmol) of chloro-bis(3,5-di(trifluoromethyl)-phenyl)phosphane. Working up, purification and crystallization as described in Example 3 gave 3.55 g (64%) of (S)-N-[bis(3,5-di(trifluoromethyl)phenyl)-phosphanyl]-2-[(bis(3,5-di(trifluoromethyl)phenyl-phosphanyl)oxy]-3,3,N-trimethyl-butyramide [(S)-3,5-CF$_3$-tLANOP] as a light brown, hydrolysis-sensitive oil. Purity: about 90% (NMR), $^{31}$P-NMR (δ, ppm): 50.8 (P-N), 112.9 (P-O).

Example 10

Preparation of (R)-N-[bis(3,5-di(tert. butyl)phenyl)-phosphanyl]-2-[(bis(3,5-di(tert. butyl)phenyl)-phosphanyl)oxy]-3,3,N-trimethyl-butyramide Analogously to the synthesis described in Example 3, a mixture consisting of 0.68 g (4.74 mmol) of (R)-2-hydroxy-3,3,N-trimethyl-butyramide, 0.05 ml of diisopropylamine and 5.93 ml (9.48 mmol) of butyllithium in tetrahydrofuran was treated at about −78° C. with 4.22 g (9.48 mmol) of chloro-bis(3,5-di-(tert. butyl)phenyl)phosphane. Working up, purification and crystallization as described in Example 3 gave 3.78 g (83%) of (R)-N-[bis(3,5-di(tert. butyl)phenyl)-phosphanyl]-2-[(bis(3,5-di(tert. butyl)phenyl)-phosphanyl)oxy]-3,3,N-trimethyl-butyramide [(R)-3,5-tBu-tLANOP] as a colorless powder after crushing with a spatula. Purity: about 95% (NMR). $^{31}$P-NMR (δ, ppm): 56.4 (P-N), 112.4 (P-O).

Example 11

Preparation of (S)-N-[bis(3,5-di(tert. butyl)phenyl)-phosphanyl]-2-[(bis(3,5-di(tert. butyl)phenyl)-phosphanyl)oxy]-3,3,N-trimethyl-butyramide Analogously to the synthesis described in Example 3, a mixture consisting of 0.93 g (6.4 mmol) of (S)-2-hydroxy-3,3,N-trimethyl-butyramide, 0.05 ml of diisopropylamine and 8.00 ml (12.8 mmol) of butyllithium in tetrahydrofuran was treated at about −78° C. with 5.99 g (12.8 mmol) of chloro-bis(3,5-di-(tert. butyl)phenyl)phosphane. Working up, purification and crystallization as described in Example 3 gave 3.41 g (3.54 mmol, 55%) of (S)-N-[bis(3,5-di(tert. butyl)phenyl)-phosphanyl]-2-[(bis(3,5-di(tert. butyl)phenyl)phosphanyl)oxy]-3,3,N-trimethyl-butyramide [(S)-3,5-tBu-tLANOP] as a colorless powder. Purity: about 97% (NMR). $^{31}$P-NMR (δ, ppm): 56.4 (P-N), 112.4 (P-O).

Example 12

Preparation of (S)-N-[bis(3,5-di(tert. butyl)-4-methoxyphenyl)-phosphanyl]-2-[(bis(3,5-di(tert. butyl)-4-methoxyphenyl)-phosphanyl)oxy]-3,3,N-trimethylbutyramide Analogously to the synthesis described in Example 3, a mixture consisting of 0.59 g (4.07 mmol) of (S)-2-hydroxy-3,3,N-trimethyl-butyramide, 0.05 ml of diisopropylamine and 5.08 ml (8.14 mmol) of butyllithium in tetrahydrofuran was treated at about −78° C. with 4.11 g (8.14 mmol) of chloro-bis(3,5-di-(tert. butyl)-4-methoxyphenyl)phosphane. Working up, purification and crystallization as described in Example 3 gave 2.63 g (60%) of (S)-N-[bis(3,5-di(tert. butyl)-4-methoxyphenyl)-phosphanyl]-2-[(bis(3,5-di(tert. butyl)-4-methoxyphenyl)-phosphanyl)oxy]-3,3,N-trimethyl-butyramide [(S)-3,5-tBu,4-MeO-tLANOP] as a colorless oxidation-sensitive powder. Purity: about 95% (NMR). $^{31}$P-NMR ($\delta$, ppm): 54.2 (P-N), 110.8 (P-O).

Example 13

Preparation of (S)-N-(5H-dibenzophospholyl)-2-[(5H-dibenzophospholyl)oxy]-3,3,N-trimethyl-butyramide Analogously to the synthesis described in Example 3, a mixture consisting of 2.20 g (15.2 mmol) of (S)-2-hydroxy-3,3,N-trimethyl-butyramide, 0.3 ml of diisopropylamine and 19.0 ml (30.3 mmol) of butyllithium in tetrahydrofuran was treated at about −78° C. with 6.63 g (30.3 mmol) of 5-chloro-5H-dibenzophosphol. Working up, purification and crystallization as described in Example 3 gave 4.74 g (62%) of (S)-N-(5H-dibenzophospholyl)-2-[(5H-dibenzophospholyl)oxy]-3,3,N-trimethyl-butyramide [(S)-Diphol-tLANOP] as a colorless powder. Purity: ≧90% (NMR). $^{31}$P-NMR ($\delta$, ppm): 40.4 (P-N), 112.2 (P-O).

Example 14

Preparation of [(R)-2-(1-dimethylamino-ethyl)-phenyl-C,N]-[(S)-N-(diphenylphosphanyl)-2-[(diphenylphosphanyl)oxy]-3,3-N-trimethyl-butyramide]Pd(II) tetrafluoroborate This complex serves for the characterization of the named compound of formula I.

105 mg (0.250 mmol) of bis-(acetonitrile)-[(R)-2-(1-dimethylamino-ethyl)phenyl]-Pd(II) tetrafluoroborate and 129 mg (0.250 mmol) of (S)-N-(diphenylphosphanyl)-2-[(diphenylphosphanyl)oxy]-3,3,N-trimethyl-butyramide were weighed into a 50 ml Schlenk tube having a stirring core and a serum stopper in a glove box and dissolved in 10 ml of dichoromethane. After stirring at RT for ten minutes the colorless clear solution was evaporated to dryness at RT in a HV. The colorless residue was washed with 10 ml of diethyl ether and dried in a HV for 2 hours. Yield: 211 mg (98%) of [(R)-2-(1-dimethylamino-ethyl)-phenyl-C,N]-[(S)-N-(diphenylphosphanyl)-2-[(diphenylphosphanyl)oxy]-3,3,N-trimethyl-butyramide]Pd(II) tetrafluoroborate. Purity: about 98% (NMR).

| | Microanalysis: | | |
|---|---|---|---|
| | C | H | N |
| Calc. | 57.60 | 5.54 | 3.28 |
| Found | 57.42 | 5.54 | 3.08 |

Example 15

Preparation of (cycloocta-1,5-diene)-[(R)-N-(diphenylphosphanyl)-2-[(diphenylphosphanyl)oxy]-3,3,N-trimethyl-butyamide]Rh(I) tetrafluoroborate A solution of 189 mg (0.368 mmol) of (R)-N-(diphenylphosphanyl)-28(diphenylphosphanyl)oxyl-3,3,N-trimethyl-butyramide in 10 ml of tetrahydrofuran was added dropwise while stirring at RT over 2 minutes to a suspension of 144 mg (0.355 mmol) of bis-(cycloocta-1,5-diene)-Rh(I) tetrafluoroborate in 10 ml of tetrahydrofuran in a 100 ml Schienk tube. Thereby the orange-brown suspension changed immediately into a clear yellow-orange solution which, after stirring for 5 minutes, was evaporated in a HV at RT. After drying in a HV for 2 hours the residual orange oily residue was suspended in 10 ml of diethyl ether, the supernatant solution was separated after standing at RT for 12 hours and the yellow finely crystalline solid was dried in a HV for 12 hours. Yield: 278 mg (97%) of (cycloocta-1,5-diene)-[(R)-N-(diphenylphosphanyl)-2-[(diphenylphosphanyl)oxy]-3,3,N-trimethyl-butyramide]Rh(I) tetrafluoroborate. Purity: ≧99% (NMR).

| | Microanalysis: | | | |
|---|---|---|---|---|
| | C | H | N | P |
| Calc. | 57.73 | 5.59 | 1.73 | 7.63 |
| Found | 57.51 | 5.59 | 1.46 | 7.41 |

Example 16

Preparation of (cycloocta-1,5-diene)-[(S)-N-(diphenylphosphanyl)-2-[(diphenylphosphanyl)oxyl]-3,3,N-trimethyl-butyramide]Ir(I) tetra-fluoroborate Analogously to the synthesis described in Example 15, a mixture consisting of 96 mg (0.195 mmol) of bis-(cycloocta-1,5-diene)-Ir(I) tetra-fluoroborate and 100 mg (0.195 mmol) of (S)-N-(diphenylphosphanyl)-2-[(diphenylphosphanyl)oxy]-3,3,N-trimethyl-butyramide in 20 ml of tetrahydrofuran was stirred at RT for 30 minutes. Working up and crystallization as described in Example 15 gave 139 mg (80%) of (cycloocta-1,5-diene)-[(S)-N(diphenylphosphanyl)-2-[(diphenylphosphanyl)oxy]-3,3,N-trimethyl-butyramide]Ir(I) tetrafluoroborate as red crystals. Purity: ≧99% (NMR).

| | Microanalysis: | | | |
|---|---|---|---|---|
| | C | H | N | P |
| Calc. | 52.00 | 5.04 | 1.56 | 6.88 |
| Found. | 51.93 | 4.95 | 1.51 | 6.43 |

Example 17

Catalytic hydrogenation of 1-(4-methoxybenzyl)-3,4,5,6,7,8-hexahydroisoquinoline tetrafluoroborate 13.4 mg (0.020 mmol) of [IrCl(COD)]$_2$ and 57.7 mg (0.060 mmol) of (R)-3,5-tBu-tLANOP as the chiral ligand were dissolved in 4 ml of toluene in a 35 ml autoclave having a glass attachment in a glove box (O$_2$ content<1 ppm). After adding 59.1 mg (0.16 mmol) of tetrabutylammonium iodide (Bu$_4$N$^+$I$^-$) and stirring for 30 minutes 0.343 g (1.0 mmol) of 1-(4-methoxybenzyl)-3,4,5,6,7,8-hexahydroisoquinoline tetrafluoroborate and 4 ml of methanol were added to this catalyst solution. Then the autoclave was sealed and the hydrogenation was carried out while stirring at 25° C. and at a hydrogen pressure of 100 bar (10 MPa) for 44 hours. The yellow hydrogenation solution was evaporated on a rotary evaporator at 40° C./20 mbar (2 kPa). With a complete conversion the residue consisted, according to HPLC [column: ChiralPAK AD (Daicel Chem. Ind. Ltd.; catalogue No. 7407-00), eluent: 10% ethanol and 0.2% triethylamine in hexane] and GC [as the (−)-camphanic acid amide, column: OV-240 OH (Ohio Valley Chemicals, Marietta, Ohio, USA; catalogue No. 091785) 15 m] analysis, of 48% (S)-1-(4-methoxybenzyl)-1,2,3,4,5,6,7,8-octahydroisoquinoline with an ee of 72%.

Examples 17.1–17.7

The hydrogenation of 1-(4-methoxybenzyl)-3,4,5,6,7,8-hexahydroisoquinoline HX salts with the chiral ligands set forth in Table 1 was carried out in an analogous manner to Example 17. The experiments with HX=HBF$_4$ and HPF$_6$ were carried out in toluene (4 ml)/methanol (4 ml) and those with HX=H$_2$SO$_4$ were carried out in tetrahydrofuran (8 ml)/water (0.2 ml).

TABLE 1

| Ex. No. | HX | Chiral ligand | % Selectivity | % ee |
|---|---|---|---|---|
| 17.1[a] | HBF$_4$ | (R)-3,5-tBu-tLANOP | 55 | 67 (R) |
| 17.2[b] | HBF$_4$ | " | 80 | 65 (R) |
| 17.3 | HBF$_4$ | (S)-3,5-tBu,4-MeO-tLANOP | 55 | 78 (S) |
| 17.4 | H$_2$SO$_4$ | (S)-3,5-tBu-tLANOP | 46 | 86 (S) |
| 17.5[a] | H$_2$SO$_4$ | (R)-3,5-tBu-tLANOP | 36 | 73 (R) |
| 17.6[c] | H$_2$SO$_4$ | (R)-3,5-tBu-tLANOP | 66 | 70 (R) |
| 17.7 | HPF$_6$ | (S)-3,5-tBu,4-MeO-tLANOP | 52 | 78 (S) |

[a] Addition of 0.026 mmol of BiI$_3$ in place of Bu$_4$N$^+$I$^-$;
[b] addition of 0.08 mmol of phthalimide in place of Bu$_4$N$^+$I$^-$;
[c] temperature = 80° C., S/C; 5000;

Examples 18.1 and 18.2

Catalytic hydrogenation of 4-acetoxy-2,6,6-trimethylcyclohexa-2,4-dien-1-one

The hydrogenation of 4-acetoxy-2,6,6-trimethylcyclohexa-2,4-dien-1-one to 4-acetoxy-2,6,6-trimethylcyclohexa-2-en-1-one with the chiral ligands set forth in Table 2 was carried out in an analogous manner to Example 17.

TABLE 2

| Ex. No. | Substrate | Chiral ligand | Cat.[a] | % ee |
|---|---|---|---|---|
| 18.1 | 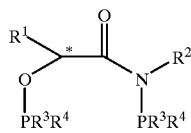 | (S)-tLANOP | Rh(BF$_4$) | 71 (R) |
| 18.2 | | (S)-Cy-tLANOP | " | 71 (R) |

[a] Rh(BF$_4$): complex prepared in situ from [Rh(COD)$_2$]BF$_4$ and the chiral ligands; conditions S/Rh 100, ethyl acetate, RT, 10 bar (1 MPa) hydrogen.

What is claimed is:

1. A compound of general formula (I):

$$\begin{array}{c} R^1 \\ \phantom{R^1}*\phantom{R^1} \\ O \phantom{xx} N-R^2 \\ | \phantom{xxxx} | \\ PR^3R^4 \phantom{x} PR^3R^4 \end{array} \quad \text{I}$$

wherein
R$^1$ is C$_{3-8}$-cycloalkyl, aryl-C$_{1-4}$-alkyl, or branched C$_{3-8}$-alkyl,
R$^2$ is C$_{1-8}$-alkyl, C$_{3-8}$-cycloalkyl, aryl-C$_{1-4}$-alkyl or aryl,
R$^3$ and R$^4$ each independently are C$_{1-8}$-alkyl, C$_{3-8}$-cycloalkyl, aryl-C$_{1-4}$- alkyl, aryl or heteroaryl or R$^3$ and R$^4$ together with a phosphorus atom are a 9-dibenzophospholyl, 9- phosphabicyclononyl or 9-phosphabicyclononyl group,

* denotes a chiral center, and
each R$^3$ is identical to the other, and each R$^4$ is identical to the other.

2. The compound of claim 1 in the (R) form.

3. The compound of claim 1 in the (S) form.

4. The compound of claim 1, wherein R$^3$ and R$^4$ are the same.

5. The compound of claim 2, wherein R$^3$ and R$^4$ are the same.

6. The compound of claim 3, wherein R$^3$ and R$^4$ are the same.

7. The compound according to claim 1, wherein R$^1$ is tert. butyl.

8. The compound according to claim 2, wherein R$^1$ is tert. butyl.

9. The compound according to claim 3, wherein R$^1$ is tert. butyl.

10. The compound according to claim 4, wherein R$^1$ is tert. butyl.

11. The compound according to claim 5, wherein R$^1$ is tert. butyl.

12. The compound according to claim 6, wherein R$^1$ is tert. butyl.

13. The compound according to claim 1, wherein R$^2$ is methyl.

14. The compound according to claim 2, wherein R$^2$ is methyl.

15. The compound according to claim 3, wherein R$^2$ is methyl.

16. The compound according to claim 4, wherein R$^2$ is methyl.

17. The compound according to claim 5, wherein R$^2$ is methyl.

18. The compound according to claim 6, wherein R$^2$ is methyl.

19. The compound according to claim 7, wherein R$^2$ is methyl.

20. The compound according to claim 8, wherein R$^2$ is methyl.

21. The compound according to claim 9, wherein R$^2$ is methyl.

22. The compound according to claim 10, wherein R$^2$ is methyl.

23. The compound according to claim 11, wherein R$^2$ is methyl.

24. The compound according to claim 12, wherein R$^2$ is methyl.

25. The compound of claim 19, wherein R$^3$ and R$^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

26. The compound of claim 20, wherein R$^3$ and R$^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

27. The compound of claim 21, wherein R$^3$ and R$^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

28. The compound of claim 22, wherein R$^3$ and R$^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

29. The compound of claim 23, wherein $R^3$ and $R^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

30. The compound of claim 24, wherein $R^3$ and $R^4$ each independently are selected from the group consisting of cyclohexyl, phenyl, 3,5-xylyl, 3,5-di(trifluoromethyl) phenyl, 3,5-di(tert. butyl)phenyl, 3,5-di(tert. butyl)-4-methoxyphenyl and 2-furyl.

31. The compound of claim 19, wherein $R^3$ and $R^4$ are each 3,5-di(tert. butyl)phenyl.

32. The compound of claim 20, wherein $R^3$ and $R^4$ are each 3,5-di(tert. butyl)phenyl.

33. The compound of claim 21, wherein $R^3$ and $R^4$ are each 3,5-di(tert. butyl)phenyl.

34. The compound of claim 22, wherein $R^3$ and $R^4$ are each 3,5-di(tert. butyl)phenyl.

35. The compound of claim 23, wherein $R^3$ and $R^4$ are each 3,5-di(tert. butyl)phenyl.

36. The compound of claim 24, wherein $R^3$ and $R^4$ are each 3,5-di(tert. butyl)phenyl.

37. The compound of claim 1 wherein, $R^3$ and $R^4$ together with said phosphorus atom signify 9-dibenzophospholyl.

38. A compound of the general formula:

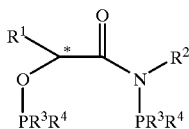

I wherein
$R^1$ is tert. butyl,
$R^2$ is methyl, and
$R^3$ and $R^4$ each are 3,5-di(tert.butyl)phenyl, and
* denotes a chiral center.

39. A compound according to claim 1, (S)-N-(diphenylphosphanyl)-2-[(diphenylphosphanyl)oxy]-3,3,N-trimethyl-butyramide.

40. A compound according to claim 1, (R)-N-(diphenylphosphanyl)-2-[(diphenylphosphanyl)oxy]-3,3,N-trimethyl-butyramide.

41. A compound according to claim 1, (S)-N-[di-(2-furyl)-phosphanyl]2-[(di-(2-furyl)-phosphanyl)oxy]-3,3,N-trimethyl-butyramide.

42. A compound according to claim 1, (R)-N-[di-(2-furyl)-phosphanyl]2-[(di-(2-furyl)-phosphanyl)oxy]-3,3,N-trimethyl-butyramide.

43. A compound according to claim 1, (S)-N-(dicyclohexylphosphanyl)-2-[(dicyclohexylphosphanyl) oxy]-3,3,N-trimethyl-butyramide.

44. A compound according to claim 1, (R)-N-(dicyclohexylphosphanyl)-2-[(dicyclohexylphosphanyl) oxy]-3,3,N-trimethyl-butyramide.

45. A compound according to claim 1, (S)-N-[bis(3,5-dimethylphenyl)phosphanyl]-2-[(bis(3,5-dimethylphenyl)-phosphanyl)oxy]-3,3,N-trimethyl-butyramide.

46. A compound according to claim 1, (R)-N-[bis(3,5-dimethylphenyl)-phosphanyl]-2-[(bis(3,5-dimethylphenyl)-phosphanyl)oxy]-3,3,N-trimethyl-butyramide.

47. A compound according to claim 1, (S)-N-[bis(3,5-di (tert. butyl)phenyl)-phosphanyl]-2-[(bis(3,5-di-(tert. butyl) phenyl)-phosphanyl)oxy]-3,3,N-trimethyl-butyramide.

48. A compound according to claim 1, (R)-N-[bis(3,5-di (tert.butyl)phenyl)-phosphanyl]-2-[(bis(3,5-di-(tert. butyl) phenyl)-phosphanyl)oxy]-3,3,N-trimethyl-butyramide.

49. A compound according to claim 1, (S)-N-[bis(3,5-di (tert. butyl)-4-methoxyphenyl)-phosphanyl]-2-[(bis(3,5-di (tert. butyl)-4-methoxyphenyl)phosphanyl)oxy]-3,3,N-trimethyl-butyramide.

50. A compound according to claim 1, (R)-N-[bis(3,5-di (tert. butyl)-4-methoxyphenyl)-phosphanyl]-2-[(bis(3,5-di (tert. butyl)-4-methoxyphenyl)-phosphanyl)oxy]-3,3,N-trimethyl-butyramide.

51. A compound according to claim 1, (S)-N-(5H-dibenzophospholyl)-2-[(5H-dibenzophospholyl)oxy]-3,3,N-trimethyl-butyramide.

52. A compound according to claim 1, (R)-N-(5H-dibenzophospholyl)-2-[(5H-dibenzophospholyl)oxy]-3,3,N-trimethyl-butyramide.

53. A compound according to claim 1, (S)-N-[bis(3,5-di (trifluoromethyl)phenyl)-phosphanyl]-2-[(bis(3,5-di (trifluoromethyl)phenyl)-phosphanyl)oxy]-3,3,N-trimethyl-butyramide.

54. A compound according to claim 1, (R)-N-[bis(3,5-di (trifluoromethyl)phenyl)-phosphanyl]-2-[(bis(3,5-di (trifluoromethyl)phenyl)-phosphanyl)oxy]-3,3,N-trimethyl-butyramide.

* * * * *

UNITED STATES PATENT AND TRADEMARK OFFICE
CERTIFICATE OF CORRECTION

PATENT NO.    : 6,348,612 B1
DATED         : February 19, 2002
INVENTOR(S)   : Wolfgang Burkart et al.

It is certified that error appears in the above-identified patent and that said Letters Patent is hereby corrected as shown below:

<u>Column 14,</u>
Line 2, please change "phosphabicyclononyl" to -- phosphabicyclo[3.3.1]nonyl --;
Lines 2-3, please change "9-phosphabicyclononyl" to -- 9-phosphabicyclo[4.2.1]nonyl --;

<u>Column 15,</u>
Line 47, please change "phosphanyl]2" to -- phosphanyl]-2 --;

<u>Column 16,</u>
Line 2, please change "phosphanyl]2" to -- phosphanyl]-2 --.

Signed and Sealed this

Fifteenth Day of October, 2002

JAMES E. ROGAN
*Director of the United States Patent and Trademark Office*

*Attest:*

*Attesting Officer*